United States Patent
Bonmassar et al.

(10) Patent No.: US 8,944,985 B2
(45) Date of Patent: Feb. 3, 2015

(54) DEEP BRAIN STIMULATION IMPLANT WITH MICROCOIL ARRAY

(75) Inventors: Giorgio Bonmassar, Lexington, MA (US); Matti S. Hamalainen, Boston, MA (US); Bruce Rosen, Lexington, MA (US)

(73) Assignee: The General Hospital Corporation, Boston, MA (US)

( * ) Notice: Subject to any disclaimer, the term of this patent is extended or adjusted under 35 U.S.C. 154(b) by 1330 days.

(21) Appl. No.: 12/418,324

(22) Filed: Apr. 3, 2009

(65) Prior Publication Data
US 2009/0254146 A1 Oct. 8, 2009

Related U.S. Application Data

(60) Provisional application No. 61/042,070, filed on Apr. 3, 2008.

(51) Int. Cl.
| | |
|---|---|
| *A61N 1/00* | (2006.01) |
| *A61N 2/02* | (2006.01) |
| *A61N 2/00* | (2006.01) |
| *A61N 1/36* | (2006.01) |
| *A61N 1/05* | (2006.01) |
| *A61N 1/40* | (2006.01) |

(52) U.S. Cl.
CPC ............... *A61N 2/004* (2013.01); *A61N 2/006* (2013.01); *A61N 1/36082* (2013.01); *A61N 2/02* (2013.01); *A61N 1/0534* (2013.01); *A61N 1/40* (2013.01); *A61N 1/0531* (2013.01)
USPC .............................................. 600/13; 607/116

(58) Field of Classification Search
USPC ............... 600/9–15, 372, 373, 377, 378, 393; 606/32–52; 607/1, 41, 45, 46, 607/115–118, 148
See application file for complete search history.

(56) References Cited

U.S. PATENT DOCUMENTS

| | | | |
|---|---|---|---|
| 4,969,468 A | * | 11/1990 | Byers et al. .................. 600/373 |
| 5,133,710 A | | 7/1992 | Carter, Jr. et al. |
| 5,366,496 A | | 11/1994 | Dahl et al. |
| 6,301,492 B1 | | 10/2001 | Zonenshayn |
| 6,920,359 B2 | | 7/2005 | Meadows et al. |
| 7,010,356 B2 | | 3/2006 | Jog et al. |
| 7,177,701 B1 | | 2/2007 | Pianca |
| 7,212,851 B2 | | 5/2007 | Donoghue et al. |
| 7,285,118 B1 | | 10/2007 | Lozano |
| 7,407,478 B2 | | 8/2008 | Zangen et al. |
| 2002/0161403 A1 | | 10/2002 | Meadows et al. |

(Continued)

OTHER PUBLICATIONS

J. Ruohonen, R. J. Ilmoniemi, "Focusing and targeting of magnetic brain simulation using multiple coils," Medical & Biological Engineering & Computing, May 1998, pp. 297-301.

(Continued)

*Primary Examiner* — Charles A Marmor, II
*Assistant Examiner* — Carrie R Dorna
(74) *Attorney, Agent, or Firm* — Quarles & Brady, LLP

(57) ABSTRACT

An implant for deep brain stimulation (DBS) has an array of electromagnetic microcoils dispersed over the length of the implant. The microcoils produce magnetic fields that are directed into, and induce current in, the adjacent brain tissue. The microcoils may be selectively operated to direct and focus electrical stimulation to targeted areas of the brain. The implant is useful in studying or treating neurophysiological conditions associated with the deep regions of the brain such as Parkinson's disease, drug addiction, and depression.

22 Claims, 2 Drawing Sheets

(56) References Cited

U.S. PATENT DOCUMENTS

| | | |
|---|---|---|
| 2005/0055064 A1 | 3/2005 | Meadows et al. |
| 2005/0275497 A1 | 12/2005 | Ramadan et al. |
| 2006/0074450 A1 | 4/2006 | Boveja et al. |
| 2006/0095105 A1 | 5/2006 | Jog et al. |
| 2006/0184209 A1 | 8/2006 | John et al. |
| 2006/0276866 A1* | 12/2006 | McCreery .................. 607/116 |
| 2007/0027501 A1 | 2/2007 | Jensen et al. |
| 2007/0027514 A1 | 2/2007 | Gerber |
| 2007/0027515 A1 | 2/2007 | Gerber |
| 2007/0106143 A1 | 5/2007 | Flaherty |
| 2008/0269854 A1 | 10/2008 | Hegland et al. |

OTHER PUBLICATIONS

J. M. Henderson, J. Tkach, M. Phillips, K. Baker, F. G. Shellock, A. R. Rezai, "Permanent Neurological Deficit Related to Magnetic Resonance Imaging in a Patient With Implanted Deep Brain Stimulation Electrodes for Parkinson's Disease: Case Report," Neurosurgery, vol. 57, No. 5, Nov. 2005.

J. Moulin, M. Woytasik, E. Martincic, E. Dufour-Gergam, "Copper Planar Microcoils Applied to Magnetic Actuation," DTIP 2007, Stresa, Italy, Apr. 25-27, 2007.

* cited by examiner

DEEP BRAIN STIMULATION IMPLANT WITH MICROCOIL ARRAY

CROSS-REFERENCE TO RELATED APPLICATIONS

This application is based on, fully incorporates herein by reference, and claims the benefit of U.S. Provisional Application Ser. No. 61/042,070, filed on Apr. 3, 2008, and entitled "DEEP BRAIN STIMULATION IMPLANT WITH MICRO MAGNETIC STIMULATION ARRAY".

STATEMENT REGARDING FEDERALLY SPONSORED RESEARCH

This invention was made with government support under HD044425 awarded by the National Institutes of Health. The government has certain rights in the invention.

BACKGROUND OF THE INVENTION

The present invention relates to deep brain stimulation (DBS) systems to treat certain medical conditions and, more particularly, to an implantable device having an array of selectively operable electromagnetic microcoils to induce currents in surrounding brain tissue.

Over 50,000 Americans are diagnosed with Parkinson's disease each year, with more than half a million Americans affected at any given time. Conventional treatments include pharmaceutical agents that produce dopamine, a neurotransmitter, in an attempt to replenish the low levels found in the brains of those suffering from the disease. Approximately ten percent of people with Parkinson's disease initially treated with pharmaceutical agents have little to no response. Electrical stimulation of the brain presents an alternative treatment option.

Specifically, deep brain stimulation has been used to effectively treat the symptoms of Parkinson's disease including rigidity, slowed movements, tremors, and walking difficulties. DBS treatment involves the surgical implantation of an electrical stimulator, often referred to as an electrode, lead, or implant, in the basal ganglia. Depending on the observed symptoms and treatment plan, DBS implants may be used to provide unilateral or bilateral simulation in the subthalamic nucleus (STN) or in the globus pallidus internus (GPi).

Existing DBS systems include one or more implants having a limited number of electrodes, a programmable current or voltage pulse generator, a battery, and electrical leads. Electrical impulses are created by the pulse generator, directed to the implants via the electrical leads, and continuously delivered to the STN or GPi brain sites via the electrodes up to twenty four hours per day.

The technology associated with DBS systems has the potential to help people afflicted with other physical ailments shown to respond to electrical stimulation. For example, stimulation of the brain's motor cortical areas has been used to help ischemic stroke survivors regain partial use of a weakened hand or arm. Further, it has been suggested that cortical brain stimulation can be successfully used to treat epilepsy. Other neurological disorders may also be treated with stimulation outside of the brain.

In spite of the clinical and potential successes, existing deep brain stimulation systems have a number of drawbacks. One drawback is the poor spatial resolution of existing DBS implants. Conventional cylindrical DBS implants have a very limited number of electrodes per implant because of spatial requirements between electrodes to prevent electrophoresis. Because of these gaps between electrodes, electrical stimulation of the brain may not be optimized. Further, during placement and setup of a DBS implant, a large variability exists between the location and size of the stimulation area within the brain and the amount of current to be delivered. Although numerical tools have been developed to estimate the volume of tissue activated (VTA) by each electrode, each DBS implant must still be positioned and set up on a case-by-case basis.

A second drawback of existing DBS systems is the large size requirement for electrodes in order to limit the effects of high current densities and electrophoresis. One conventional DBS implant includes cylindrical electrodes with a radius of 0.5 millimeters and a length of 2.5 millimeters. In practice, the dimension of each electrode is roughly equal to the portion of the brain intended to be stimulated, thus limiting the flexibility for spatially selective stimulation of the brain.

A third drawback of existing DBS systems is the use of copper-containing electrical leads between the pulse generator and the electrodes. These leads are not compatible with magnetic resonance imaging (MRI) procedures and special precautions must be adhered to during MRI procedures. While copper is not a ferromagnetic material and thus, the electrodes do not move or become dislodged when subjected to strong magnetic fields, large electrical currents may nonetheless be induced resulting in thermal damage to the brain tissue. DBS implants with elongated configurations or that are electronically activated are particularly prone to having induced currents.

Efforts have been made to overcome these and other drawbacks of existing DBS implants. Micro- and nano-electrodes, for example, may overcome the poor spatial stimulation characteristics of existing DBS implants and deliver currents into targeted brain regions to provide a more accurate physiological localization and stimulation. However, these implants still use capacitive coupling to deliver an electric current and thus, do not overcome the problems associated with direct electrode-to-tissue contact.

Transcranial magnetic stimulation (TMS), overcomes the problems of direct electrode-to-tissue contact by utilizing a non-invasive treatment. TMS devices utilize Faraday's law of electromagnetic induction that a changing magnetic field can induce electric current to flow in any conductive structure, including human tissue. TMS devices operate by passing a brief electrical pulse through one or more electrically conductive coils positioned adjacent to the human skull. The coils produce magnetic fields at right angles from the coils, through the skull, and into the brain. The magnetic fields, in turn, induce electric fields in the brain tissue to stimulate the nerves.

Although non-invasive, TMS has its own drawbacks. Because the intensity of magnetic fields produced by TMS devices decreases very rapidly away from the coil, stimulating deep regions of the brain requires very strong magnetic fields. However, high intensity electric fields (induced by the strong magnetic fields) are known to cause epileptic seizures and other neurological problems. Further, the induced electric fields are not sufficiently focused and, as a result, generalized stimulation throughout the brain may occur. Still further, the amount of electric current used to drive such TMS coils is prohibitively large.

Therefore, it would be desirable to have an apparatus that provides effective, accurate, and safe deep brain stimulation.

SUMMARY

In accordance with one aspect of the present invention, a device for stimulating biological tissue, such as when performing deep brain stimulation, includes an insertable elongated implant with a plurality of microcoils. The implant extends along a longitudinal axis and has a proximal portion and a distal portion. A plurality of electrical conductors extend along the longitudinal axis of the implant and are coupled to the plurality of microcoils. An electrically isolating barrier covers the plurality of microcoils. A coupling connects the microcoils to a power source through the plurality of electrical conductors such that the plurality of microcoils can be driven to produce magnetic fields suitable for deep brain stimulation.

In accordance with another aspect of the present invention, a brain stimulation device includes a power source configured to produce a plurality of electric pulses. The brain stimulation device further includes an implant configured to receive the plurality of electrical pulses and generate a magnetic field configured to induce an electrical field adjacent to the implant.

In accordance with yet another aspect of the present invention, a deep brain stimulation system includes an implant with a base, an electrical ground layer covering the base, an electrically insulating layer covering the ground layer, a plurality of planar microcoils operable to produce a magnetic field proximate thereto, and a biocompatible dielectric coating covering the plurality of microcoils and the electrically insulating layer. The system also includes a power source configured to power at least one of the plurality of microcoils to produce a magnetic field configured to induce an electrical current in tissue adjacent to the at least one microcoil to perform DBS.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
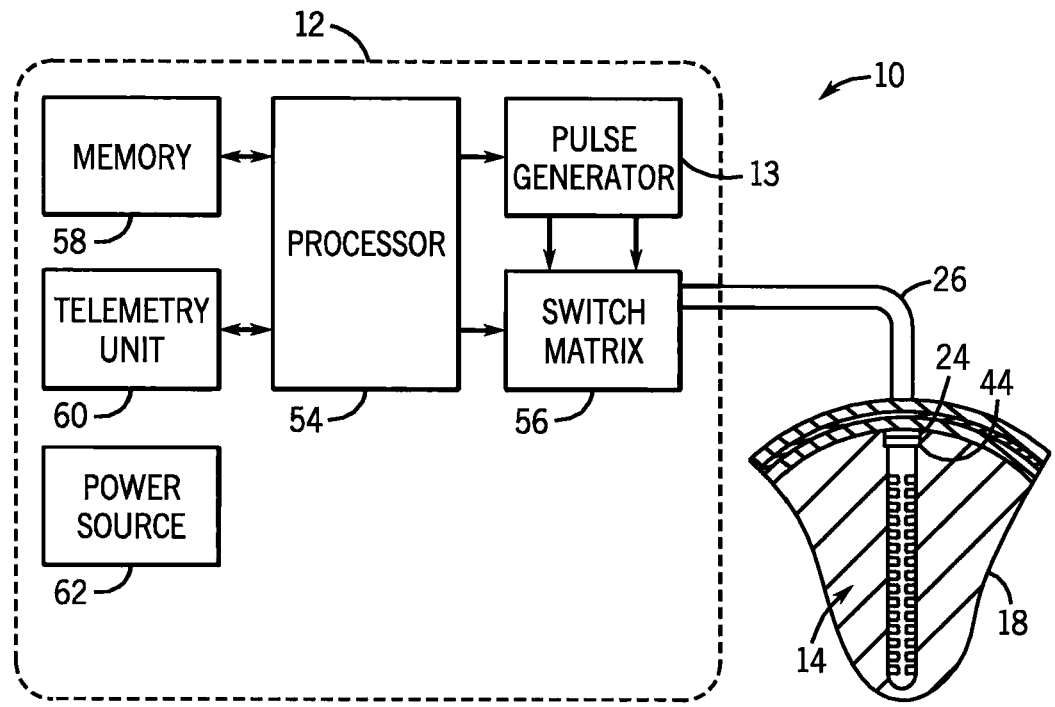
FIG. 1 is a block diagram illustrating exemplary components of a DBS system including a neurostimulator and an implant with an array of microcoils in accordance with the present invention.
Figure 2:
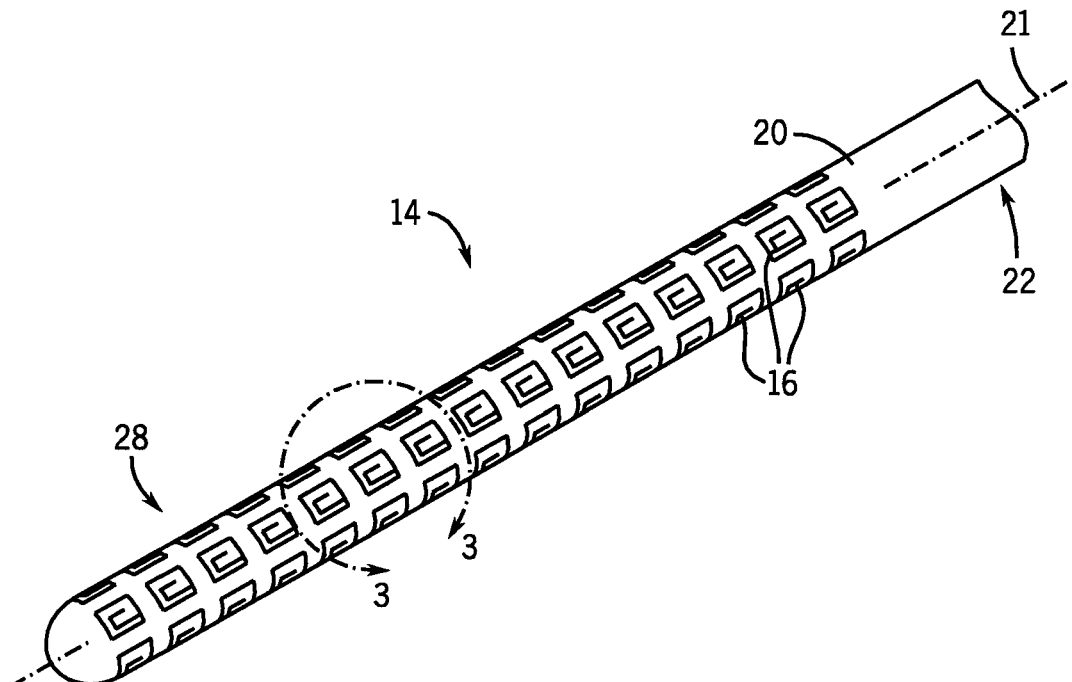
FIG. 2 is an enlarged fragmented perspective view illustrating a distal end of the implant of FIG. 1.

Referring initially to FIGS. 1 and 2, a deep brain stimulation system 10 includes a stimulator 12 coupled to an implantable device 14 (referred to hereinafter as an 'implant') with an array of planar electromagnetic microcoils 16. The stimulator 12 includes a pulse generator 13 that generates electrical pulses for delivery to a targeted stimulation site in a human brain 18 via the implant 14. The electrical pulses cause the microcoils 16 to produce magnetic fields that are directed perpendicularly into the brain 18. The magnetic fields, in turn, induce electrical currents in brain tissue to excite the neurons therein.

The implant 14 is configured as an elongated insertion probe with a narrow cylindrical shaft 20 defining a longitudinal axis 21. The shaft 20 includes a proximal portion 22 with a connector 24 coupled to the stimulator 12 via a pair of leads 26 and a distal portion 28 with a plurality of spaced-apart microcoils 16. The implant 14 also includes a plurality of electrical conductors 30 (FIG. 3) and a ground layer 32 (FIG. 4) contained within the shaft 20. Each of the microcoils 16 is coupled to one of the electrical conductors 30 and to the ground layer 32.

Figure 4:
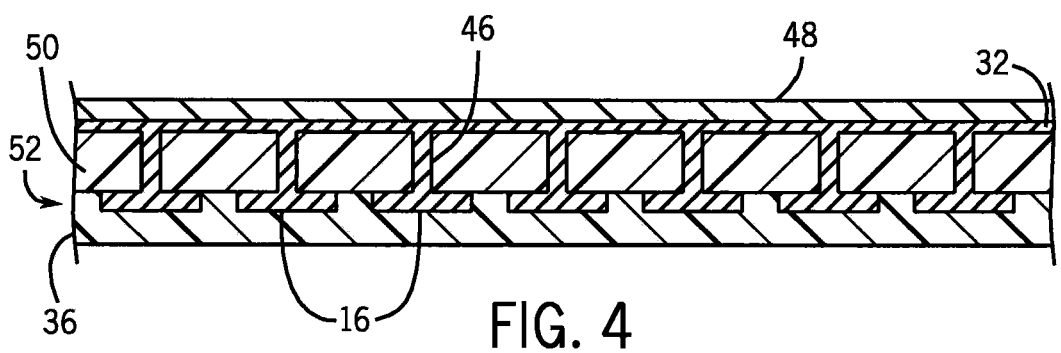
FIG. 4 is an enlarged cross sectional side view taken generally on the line 4-4 of FIG. 3.

Upon implantation of the implant 14, the microcoils 16 are positioned in close proximity to a target stimulation site for delivery of magnetic field pulses to the brain 18. Like conventional DBS implants, the implant 14 can either provoke excitation of the brain 18 or momentarily disrupt function of specific cortical regions. Unlike conventional DBS implants that have direct, capacitive contact between metal electrodes and the adjacent brain tissue, the only portion of the implant 14 in direct contact with brain tissue is a biocompatible dielectric sheath, or coating 36 (FIG. 4). Thus, the microcoils 16 are electrically isolated from the surrounding brain tissue and there is no interface therebetween.

In one configuration, the implant 14 includes a cylindrical shaft 16 with a diameter of two millimeters (2 mm) and a length of ten centimeters (10 cm). The implant 14 is designed to be surgically placed within a patient's brain 18 in a manner including, but not limited to, conventional deep brain and cortical electrode implantation techniques as discussed in greater detail below. Each microcoil 16 has an inductance of approximately 13 nH and a stray capacitance of 0.05 pF.

The actual number and arrangement of the microcoils 16 about the implant 14 may vary with specific design or application considerations and are considered to be within the scope of the present invention. Other design considerations, such as the geometry (e.g., size, shape, etc.) and placement of the microcoils 16, may be adjusted depending on the amount or location of neural stimulation for a particular treatment. The induced electric field is a sum of the electric fields induced by each microcoil, and therefore, by changing the driving currents of individual microcoils 16, the area of neural stimulation can be shaped and targeted.

Figure 3:
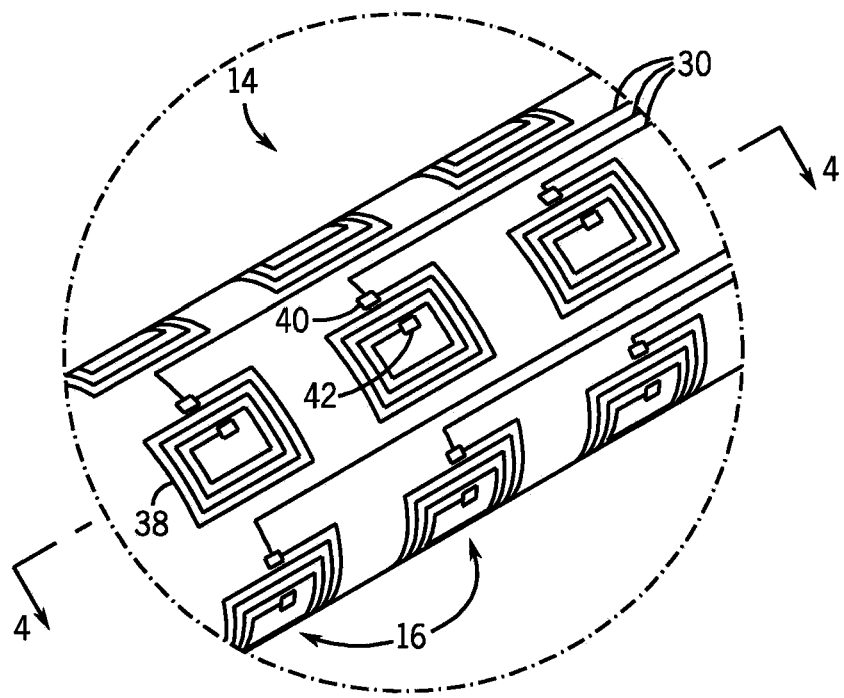
FIG. 3 is an enlarged plan view corresponding with the encircled region 3 of FIG. 2.

Referring now also to FIG. 3, microcoils 16 may be arranged across substantially the entire distal portion 28 of the implant 14. The microcoils 16 are distributed in an arrayed pattern around the shaft 20. The microcoils 16 may also be distributed in irregular patterns or have different sizes. Although the illustrated microcoils 16 are spiral-type coils formed with a continuous, multi-turn trace 38 and a have a substantially square footprint, the shape of the microcoils 16 may be circular, oval, rectangular, square, or irregular depending on the particular stimulation requirements.

Electrical connections to the microcoils 16 are made at outer bonding pads 40 and inner bonding pads 42 formed at respective ends of the multi-turn trace 38. The outer bonding pads 40 are connected to a terminal 44 at the proximal end 22 of the shaft 20 via the axially extending electrical conductors 30. The terminal 44 is coupled to the connector 24 to provide the power to the microcoils 16 via the stimulator 12 and leads 26. The inner bonding pads 42 are connected to the ground layer 32 by conductive vias 46 (FIG. 4) forming part of the electrical circuit for each microcoil 16.

FIG. 4 is a fragmented cross-sectional view showing the layers and materials of construction of the implant 14. The implant 14 includes a base 48 and at least four layers applied over the base 48 including, for example, the ground layer 32, an insulating or dielectric layer 50, a microcoil layer 52, and the biocompatible coating 36. Each of the layers are deposited onto the base 48 which may, for example, be a cylindrical glass fiber, using known deposition methods as described below.

The innermost ground layer 32 may, for example, include a three micron (3 μm) thick layer of gold uniformly deposited onto the base 48 using a conventional ion beam deposition method. The ground layer 32 provides a common current return path for each of the microcoils 16, similar to the ground plane of a typical printed circuit board.

The dielectric layer 50 may, for example, include a one hundred micron (100 μm) thick coating of insulating material such as FR-4. The FR-4 material is aerosol deposited over the ground layer 32. The conductive vias 46 formed within the dielectric layer 50 provide electrically conductive pathways between the microcoils 16 and the ground layer 32.

The microcoil layer 52 includes both the plurality of microcoils 16 and the electrical leads 14 and is situated on top of or at least partially embedded within the dielectric layer 50. In one configuration, the microcoils 16 are formed from a continuous thin film gold trace 38 and have seven turns. The microcoil 16 may be thirteen microns (13 μm) long by thirteen microns wide (13 μm) by three microns (3 μm) thick in one configuration. In this case, over one hundred microcoils 16 could fit on an implant 14 the same size as a conventional DBS implant.

The outermost biocompatible coating 36 may, for example, include a seventy-five micron (75 μm) thick coating of a biocompatible polymeric material, such as parylene. The dielectric, biocompatible material is uniformly applied via chemical vapor deposition at low pressure over the microcoils 16 and dielectric layer 50.

The use of a biocompatible polymeric material, and in particular, parylene, for the coating 36 gives the implant 14 numerous beneficial attributes. Parylene has a low coefficient of friction (e.g., 0.025) such that the implant 14 can be inserted into the brain 18 with minimal damage to adjacent brain tissue. Further, parylene has a low permeability to moisture and gases for example, 0.01% in water), thereby providing stable dielectric properties for the implant 14 over an extended period of time, which is of high importance for brain implants. Still further, parylene exhibits fungus and bacteria resistance, thereby minimizing the likelihood of an immune response. Still further, parylene exhibits high tensile and yield strength (for example, 65,000/6,300 psi), thereby reducing the potential for the coating 36 to be stripped when the implant 14 is inserted into the brain 18. Further yet, parylene exhibits increased radiation resistance which is beneficial for the sterilization of the implant 14. Finally, as previously mentioned, parylene has a high dielectric strength (for example, 7,000 V/mil@ 1 mil), thereby providing an effective electrical insulation barrier between the implant 14 and the surrounding brain tissue.

The stimulation system 10 may further include a processor 54 to set the amplitude, pulse width, and pulse rate parameters of stimulation pulses based on any of a variety of symptoms or disorders. Although the disclosed stimulator 12 and implant 14 are discussed in the context of a deep brain stimulation system 10 for alleviation of movement disorders such as Parkinson's disease, other neurological disorders such as epilepsy may beneficially treated with embodiments of the present invention. Likewise, the stimulator 12 may produce stimulation pulses with parameters selected to alleviate chronic pain, gastrointestinal disorders such as gastroparesis or obesity, and pelvic floor disorders such as incontinence, sexual dysfunction, or pain. Accordingly, the implant 14 may be fabricated for stimulation of the spinal cord, gastrointestinal tract, sacral nerves, pudendal nerves, peripheral nerves, and the like. The processor 54 may be realized by one or more microprocessors, digital signal processors (DSPs), Application-Specific Integrated Circuits (ASIC), Field-Programmable Gate Arrays (FPGA), or other equivalent integrated or discrete logic circuitry.

The stimulation system 10 may include a switch matrix 56 to apply the stimulation pulses across selected microcoils 16 within a single implant 14 or within two or more implants 14. The stimulation pulses may be applied in a bipolar or multipolar arrangement, in which multiple microcoils 16 are selected for delivery of stimulation pulses, for example, across or among different microcoil pairs or groups. Alternatively, the stimulator 12 may include multiple pulse generators 13, each coupled to and controlling a given series of microcoils 16.

A memory 58 may be provided to store instructions for execution by the processor 54 to control the pulse generator 13 and the switch matrix 56. For example, the memory 58 may be used to store programs defining different sets of stimulation parameters and microcoil combinations. Other information relating to operation of the stimulator 12 may also be stored. The memory 58 may include any form of computer-readable media such as random access memory (RAM), read only memory (ROM), electronically programmable memory (EPROM or EEPROM), flash memory, or any combination thereof.

A telemetry unit 60 supporting wireless communication between the stimulator 12 and an external programmer (not shown) may be provided. The processor 54 controls the telemetry unit 60 to receive programming information and send operational information. Programming information may be received from an external clinician programmer or an external patient programmer. The wireless telemetry unit 60 may receive and send information via radio frequency (RF) communication or proximal inductive interaction of a programmer.

A power source 62 delivers operating power to the components of the stimulator 12 including the microcoils 16. The power source 62 may include a rechargeable or nonrechargeable battery or a power generation circuit to produce the operating power. In some embodiments, battery recharging may be accomplished through proximal inductive interaction between an external charger and an inductive charging coil within the stimulator 12. In other embodiments, operating power may be derived by transcutaneous inductive power generation, e.g., without a battery.

Implant Fabrication

The fabrication process for the exemplary implant 14 includes a combination of deposition and UV micromolding techniques. In the first step, the glass fiber 48 is placed in an ion beam chamber. Gold is uniformly deposited onto the glass fiber 48 to form the ground layer 32. Subsequently, a dielectric such as FR-4 is aerosol deposited over the ground layer 32 to create the dielectric layer 50. Conductive vias 46 are formed in dielectric layer 50.

The microcoils 16 and leads 30 are fabricated in a two step process. First optical lithography is performed by applying, masking, and developing a layer of photoresist on the dielectric layer 50 to form a coil-shaped mold. Second, gold is deposited in the mold. The leads 30 extend over the length of the implant 14 between the microcoils 16 and the terminal 44. The terminal 44 may be an integral part of a suitable, medical grade connector 24, such as one produced by the Omnetics Connector Corporation of Minneapolis, Minn. Thereafter, the parylene coating 36 is vacuum deposited over the microcoils 16 and dielectric layer 50.

Computer Simulation of Exemplary Microcoil

A theoretical model of a three-turn microcoil 16 was used to calculate the magnetic field generated by such a microcoil 16 and the induced electric field in the surrounding brain tissue using a computer program. The idealized computer model used in these calculations was of a three-turn MEMs inductor coil structure. The theoretical analysis of this model was performed using the computer program Femlab®, a multiphysics modeling software application. Femlab® is a registered trademark of COMSOL AB.

The results indicated that microcoils 16 can produce electric fields sufficient to excite brain tissues even when driven by relatively small currents. For example 10 mA. In the simulation, 68,000 elements having 24,776 degrees of freedom, 680 edge elements, and 2,863 boundary elements were used. The microcoil 16 simulation model included a 680×430×600 µm block comprised of three distinct objects including a three turn microcoil made from a series of electrically connected copper traces, a dielectric material surrounding the microcoil, and a tissue substrate. The traces forming the microcoil were modeled with a thickness of 44 µm, a width of 44 µm, and varying lengths. The tissue substrate was modeled as a 680×430×200 µm block located a distance of 100 µm from the copper traces.

Femlab® was used to solve the following magnetostatics approximation of the Maxwell equations:

$$-\nabla \cdot (-\sigma v \times (\nabla \times A) + \nabla V) = 0 \quad \text{Eq. (1); and}$$

$$\nabla \times (\mu_0^{-1} \mu_r^{-1} \nabla \times A) - \sigma v \times (\nabla \times A) + \sigma \nabla v = 0 \quad \text{Eq. (2);}$$

where $\sigma$ and $\mu_r$ are the conductivity and relative permeability $\vec{A}$ is the magnetic vector potential, and V is the electric potential. The following values were used: (a) copper $\sigma_c=1e^6$ S/m, $\mu_r=1$; (b) dielectric $\sigma_c=1e^{-6}$ S/m, $\mu_r=1$; and (c) tissue $\sigma_c=0.3$ S/m, $\mu_r=1$. The permeability of a vacuum is $\mu_0=4*pi*1e-7$ H/m. All external boundaries were magnetic and electric insulation (i.e., $\vec{n} \times \vec{A}=0$ $\vec{n} \cdot \vec{J}=0$), except for the two microcoil boundaries. In these two boundaries, the first that was connected directly to the center of the microcoil was set to magnetic insulation and ground (i.e., $\vec{n} \times \vec{A}=0 V=0$) and the other boundary was set to magnetic insulation and 10 mA of inward current flow ($\vec{n} \times \vec{A}=0- \vec{n} \cdot \vec{J}=16.10^6$ A/m).

The simulations ran for 4,000 seconds on a 3.0 GHz personal computer and the results showed that an electric field having a magnitude of $|E|=1.210^5$ V/m was induced in the tissue. The simulation further showed current densities with a peak of approximately 50 A/m located directly in the tissue, suggesting that suitable excitation occurs when the microcoils 16 are situated in close proximity to neurons. Current densities in excitable tissue, such as brain tissue, above 10 A/m are known to generate a nerve response or action potential independently from the nerve axon's size. While the simulations were performed with the three-turn microcoil model, a seven-turn microcoil model may be utilized to have greater induced currents.

Computer stimulation may also be used with derived mathematical methods to simulate the effects of size, placement, and number of microcoils 16 in the array on the focality of the stimulation and on the estimated power requirements.

Implant Installation and Setup

The implant 14 may be positioned and secured into the brain 18 using an MRI system. The first step in the implantation is to non-invasively localize the patient's STN or GPi regions based on the patient's anatomical MRI scans. The second step is the functional localization of the STN or GPi sites by recording with microelectrodes at the target nucleus during surgery. The microelectrodes used for recording and stimulation mapping are guided by an MRI-based stereotactic navigation system. The desired location for the target in the STN is in the center of the motor territory. Conversely, the desired target location for the GPi is the anterolateral part of the motor territory 3-4 mm from the internal capsule. The "motor territory" can be localized using electrophysiology. The population of neurons in the STN or GPi with firing rates affected by the patient's motion (for example, an extremity) is part of the motor territory.

Next, the implant 14 is inserted at the site of the microelectrodes. The implant 14 is then set and intraoperative tests are performed to determine appropriate voltage thresholds. After the patient has recovered from surgery, postoperative imaging is used to confirm correct placement of the implant 14. Finally, permanent programming of the simulator 12 and implant 14 is performed. Importantly, the excitation of neurons in the brain tissue occurs without direct contact, and thus, the heating that may occur in prior art implants at the electrode-to-tissue interface during MR imaging procedures during MR imaging procedures does not occur with the implant 14 with microcoils 16.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

We claim:

1. A device for stimulating biological tissue, the device comprising:
   an insertable implant extending along a longitudinal axis from a proximal portion to a distal portion;
   a plurality of electrical conductors extending along the longitudinal axis of the implant;
   a plurality of microcoils proximate to the distal portion of the implant, each of the microcoils being coupled to at least one of the electrical conductors;
   an electrically isolating barrier completely covering the plurality of microcoils; and
   a coupling configured to connect the microcoils to a power source through the plurality of electrical conductors to drive the plurality of microcoils to produce magnetic fields suitable for performing deep brain stimulation (DBS).

2. The device of claim 1, wherein the distal portion of the implant is at least partially cylindrically shaped and the microcoils are spaced about the distal portion of the implant.

3. The device of claim 2, wherein the plurality of microcoils are substantially evenly spaced in an array pattern.

4. The device of claim 1, wherein the microcoils are uniformly spaced apart about the distal portion.

5. The device of claim 1, wherein each of the plurality of microcoils include at least three turns.

6. The implant of claim 1, wherein the proximal portion is configured for coupling the implant to an electrical pulse generator.

7. The device of claim 1, further comprising a stimulator configured to control a delivery of power from the power source to the plurality of microcoils to deliver an electrical current to a selected combination of the plurality of microcoils, in a preselected pattern to perform DBS.

8. The device of claim 1, wherein the implant comprises:
   a base;
   a ground layer covering the base;
   a dielectric layer covering the ground layer;
   a biocompatible coating covering the dielectric layer;
   wherein the plurality of microcoils and plurality of electrical conductors are at least one of embedded in and disposed on a radially outward surface of the dielectric layer.

9. The implant of claim 8, wherein the biocompatible coating forms at least a portion of the electrically isolating barrier covering the plurality of microcoils.

10. The implant of claim 9, wherein the biocompatible coating is parylene.

11. The implant of claim 8, wherein the base is a glass fiber and the ground layer is gold.

12. The implant of claim 1, wherein the plurality of microcoils include at least one of three-turn coils and seven-turn coils.

13. The device of claim 1, wherein each of the plurality of microcoils comprises copper.

14. A brain stimulation device comprising:
a power source configured to produce a plurality of electric pulses;
an insertable implant extending along a longitudinal axis from a proximal portion to a distal portion;
a plurality of electrical conductors extending along the longitudinal axis of the implant;
a plurality of microcoils proximate to the distal portion of the implant, each of the microcoils being coupled to at least one of the electrical conductors;
an electrically isolating barrier completely covering the plurality of microcoils; and
a coupling configured to connect the microcoils to a power source through the plurality of electrical conductors to drive the plurality of microcoils to produce magnetic fields suitable for performing deep brain stimulation (DBS).

15. The brain stimulation device of claim 14, wherein the electrically isolating barrier includes a biocompatible coating extending over the plurality of microcoils.

16. The brain stimulation device of claim 15, wherein the plurality of microcoils are formed of a gold trace and the biocompatible coating includes parylene.

17. The brain stimulation device of claim 16, wherein the plurality of microcoils are arranged in an array about the implant.

18. The brain stimulation device of claim 15, wherein at least a portion of the plurality of microcoils are disposed in a first row at a first axial position and a second row at a second axial position.

19. The brain stimulation device of claim 15, further comprising a controller configured to selectively control the delivery of the plurality of electrical pulses to the plurality of microcoils to one of focus and shape the magnetic field produced by the plurality of microcoils.

20. A deep brain stimulation system comprising:
an implant including:
a base;
an electrical ground layer covering the base;
an electrically insulating layer covering the ground layer;
a plurality of planar microcoils operable to produce a magnetic field proximate thereto; and
a biocompatible dielectric coating covering at least one of the plurality of microcoils and the electrically insulating layer; and
a power source configured to power at least one of the plurality of microcoils to produce a magnetic field configured to induce an electrical current in tissue adjacent to the at least one microcoil to perform DBS,
wherein the implant is configured such that there is no direct contact between the plurality of planar microcoils and brain tissue.

21. The system of claim 20, wherein the plurality of microcoils are spaced apart in an array over a distal portion of the implant.

22. The system of claim 20, wherein each of the plurality of planar microcoils comprises copper.

* * * * *